Dec. 7, 1954
M. P. BRISTOW
Plant Pat. 1,328
CAMELLIA PLANT
Filed April 6, 1954
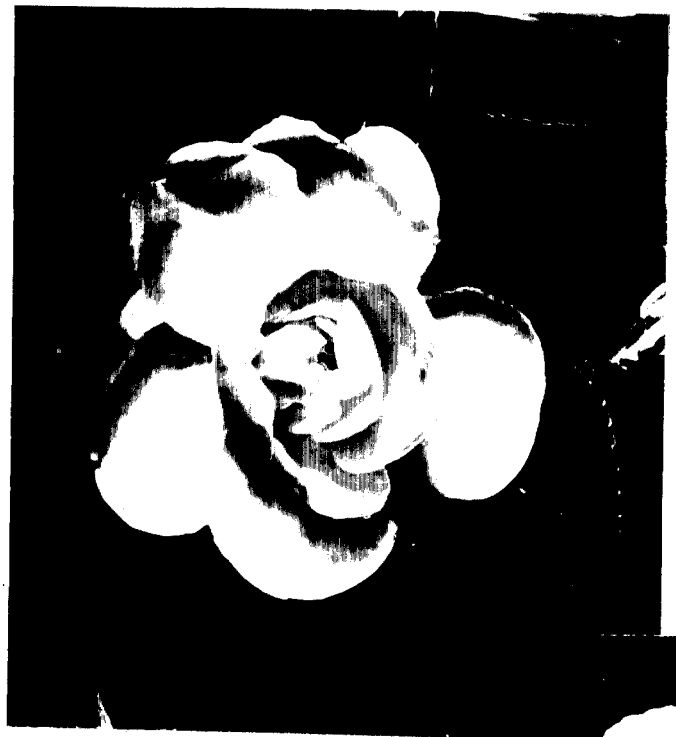
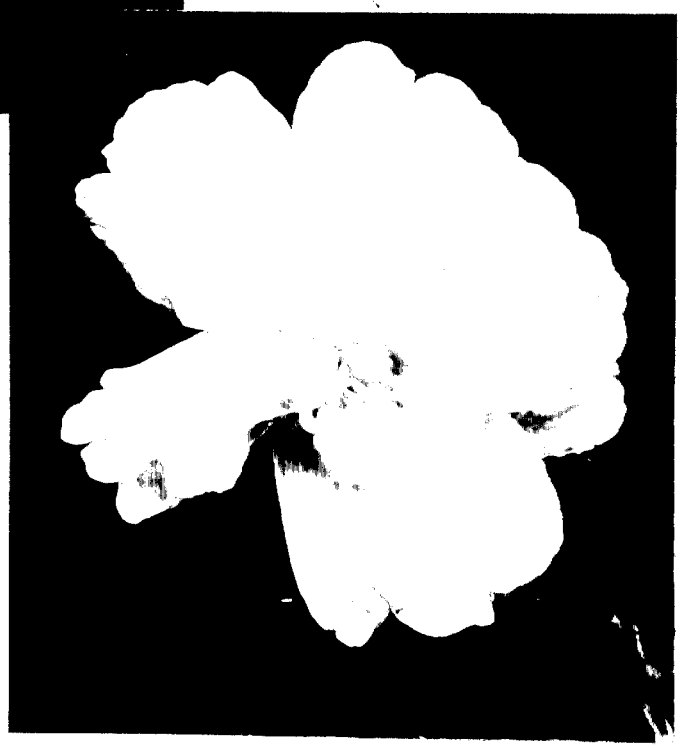
Inventor.
M. P. Bristow
By: Robert Cobb
Attorneys.

United States Patent Office

Plant Pat. 1,328
Patented Dec. 7, 1954

1,328

CAMELLIA PLANT

Maude P. Bristow, Norfolk, Va., assignor to Gulf Stream Products, Inc., Wachapreague, Va., a corporation of Virginia Application April 6, 1954, Serial No. 421,466

1 Claim. (Cl. 47—60)

The present invention relates to a new and distinct variety of camellia plant of the sasanqua or fall-blooming class, which was originated by me by crossing the variety "Sasanqua Rosea" (unpatented) with the variety "Mine-No-Yuki" (unpatented), the latter variety being known in the United States as "Snow-on-the-Mountain."

As the result of this breeding, I have produced a new variety of camellia plant which is primarily characterized as to novelty by the semi-double form, large size and distinctive pink general color tonality of its flowers. In addition to these characteristics, my new variety is unique by reason of the habit of its flowers in partially closing at night, with consequent improved weather protection and superior lasting quality on the bush.

So far as I am aware, the only other semi-double camellia of the sasanqua or fall-blooming type now available in commerce is the parent variety "Mine-No-Yuki" which bears flowers of white color, as distinguished from the pink color of the flowers of my new variety. The other parent variety, "Sasanqua Rosea," bears single type flowers of rose-red color, and although the flowers of that parent variety are highly attractive, particularly in the fall and early winter when there are few or no other colorful flowers in bloom, my new variety is much more attractive and more colorful than either parent.

Most other camellia varieties which are commercially available are of the japonica type, which bloom in the spring, and consequently, my new variety fulfills a long-felt want for a showy, full-flowered, fall-blooming camellia.

The foregoing characteristics and distinctions definitely differentiate my new variety from its parents, as well as from all other varieties, and asexual reproduction of my new variety by grafting, as performed at Norfolk, Virginia, shows that these characteristics and distinctions come true to form and are established and transmitted through succeeding propagations.

The accompanying drawing shows typical specimens of the flowers and foliage of my new variety, as depicted in color as nearly true as it is reasonably possible to make the same in a color illustration of this character, and with the flowers shown in partially-open and fully-open stages of development.

The following is a detailed description of my new variety, as based upon observations made from specimens grown at Norfolk, Virginia, with color terminology in accordance with Ridgway's Color Standards and Nomenclature, except where general color terms of ordinary dictionary significance are obvious:

Parentage: Seedling.
- *Seed parent.*—"Sasanqua Rosea."
- *Pollen parent.*—"Mine-No-Yuki."

Propagation: Holds its distinguishing characteristics through succeeding propagations by grafting.

Blooming habit: Date—October, November and December.

Bud:
- *Size.*—Medium.
- *Form.*—Globular.
- *Sepals.*—Smooth edge.
- *Calyx.*—Shape—pear. Size—small.

Bloom:
- *Size (when fully open).*—Medium; from 3½ inches to 4½ inches in diameter.
- *Borne.*—Singly; on strong stems; blooms are distributed along the branches.
- *Form.*—When first petal opens—rose form. When fully open—semi-double.
- *Blooming habit.*—Blooms develop from tight buds to tight cup-shaped, partially open flowers resembling half-open rosebuds, and finally becoming wide open.
- *Petalage.*—Semi-double; petals arranged regularly; from 15 to 18 petals.
- *Color.*—Young flowers: outer petals—Rose color, Plate XII, shading to La France Pink, Plate I at base, with Geranium Pink, Plate I veins; center petals—Rose color, Plate XII, with highlight Geranium Pink, Plate I, and depth Rose Doree, Plate I. Old flowers: La France Pink, Plate I, shading to Thulite Pink, Plate XXVI, and Spinel Pink, Plate XXVI; depth color at center Geranium Pink, Plate I; veins Geranium Pink, Plate I.
- *General color tonality.*—Pink.

Petals: Soft; with inside iridescent and outside velvety.
- *Shape.*—Ovate.
- *Arrangement.*—Regular.
- *Lasting quality.*—On plant—from 5 to 7 days. As cut flowers—several days.

Genital organs:
- *Stamens, anthers.*—Size—medium. Arrangement—regular; interspersed with 1 or 2 petaloids or "rabbit ears." Color—Empire Yellow, Plate IV.
- *Stamens, filaments.*—Medium length. Color—lemon yellow.
- *Pollen.*—Color—gold.
- *Styles.*—Bunched; even; medium length. Color—yellow with green tone.
- *Ovaries.*—All enclosed in calyx.

Fruit:
- *Form.*—Round.
- *Aspect.*—Hairy.
- *Color (at maturity).*—Gray-brown.
- *Sepals.*—Caducous; pear-shaped.

Plant:
- *Form.*—Shrub.
- *Growth.*—Vigorous; upright.
- *Foliage.* — Size — medium. Quantity — normal. Color—Empire Green, Plate XXXII. Shape—oval-pointed. Texture—upper side—glossy. Under side—smooth. Ribs and veins—ordinary. Edge—serrated. Stems—color—from Shamrock Green, Plate XXXII to Prussian Red, Plate XXVII.
- *Wood.*—New wood—color—very light brown. Old wood—color—dark gray.

I claim:

A new and distinct variety of camellia plant of the sasanqua or fall-blooming class, substantially as herein shown and described, characterized particularly as to novelty by the semi-double form, large size and distinctive pink general color tonality of its flowers, and by the habit of its flowers in partially closing at night, with consequent improved weather protection and superior lasting quality on the plant.

No references cited.